United States Patent [19]
Yamamoto

[11] Patent Number: 5,987,273
[45] Date of Patent: Nov. 16, 1999

[54] TONER CONCENTRATION DETECTING METHOD AND SYSTEM

[75] Inventor: Shinya Yamamoto, Niigata, Japan

[73] Assignee: NEC Corporation, Tokyo, Japan

[21] Appl. No.: 09/135,525

[22] Filed: Aug. 18, 1998

[30] Foreign Application Priority Data

Aug. 18, 1997 [JP] Japan ................................... 9-221669

[51] Int. Cl.$^6$ .......................... G01N 27/00; G03G 15/10
[52] U.S. Cl. .................. 399/58; 399/30; 399/62
[58] Field of Search .................. 399/27, 29, 30, 399/53, 57, 58, 59, 61, 62–65, 233, 237, 64; 430/117–119

[56] References Cited

U.S. PATENT DOCUMENTS

| | | | |
|---|---|---|---|
| 4,193,683 | 3/1980 | Langner | 399/237 |
| 4,634,252 | 1/1987 | Jeremijevic | 399/237 X |
| 4,976,901 | 12/1990 | Beck et al. | 264/45.9 |
| 5,003,352 | 3/1991 | Duchesne et al. | 399/62 X |
| 5,036,365 | 7/1991 | Landa | 399/237 |
| 5,369,476 | 11/1994 | Bowers et al. | 399/57 X |

FOREIGN PATENT DOCUMENTS 3-295453 12/1991 Japan.
8-297108 11/1996 Japan.

*Primary Examiner*—Arthur T. Grimley
*Assistant Examiner*—Quana Grainger
*Attorney, Agent, or Firm*—Young & Thompson

[57] ABSTRACT

A method for detecting a toner concentration of a liquid developer including toner particles and carrier liquid is disclosed. The carrier liquid is separated from the liquid developer and a developer electrical conductivity and a carrier liquid electrical conductivity are detected. The toner concentration is detected based on a difference of the developer electrical conductivity and a carrier liquid electrical conductivity.

18 Claims, 3 Drawing Sheets

TONER CONCENTRATION DETECTING METHOD AND SYSTEM

BACKGROUND OF THE INVENTION

1. Field of the Invention

The present invention generally relates to toner concentration control technique for use in electrophotographic equipment.

2. Description of the Related Art

Detection of toner concentration using the electric conductivity of liquid developer has been proposed in in Japanese Patent Unexamined Publication No. 3-295453. The electric conductivity is measured using alternating current because measurement using direct current causes movement of ion carriers and polarization which causes voltage drops around the electrodes. The measurement frequency is determined depending on the frequency response of the object. In the case of liquid developer, a frequency of 1 kHz may be preferably used.

However, the number of ionic contaminants or the like increases due to deterioration of liquid developer. Such ionic contaminants become a factor that substantially influences the measurement, resulting in a lower degree of measurement accuracy.

SUMMARY OF THE INVENTION

An object of the present invention is to provide a toner concentration detecting method and system which can measure the toner concentration with high accuracy.

Another object of the present invention is to provide a toner concentration controller which can keep the toner concentration optimally According to an aspect of the present invention, carrier liquid is separated from liquid developer and a developer electrical conductivity and a carrier liquid electrical conductivity are detected. The toner concentration is detected based on a difference of the developer electrical conductivity and a carrier liquid electrical conductivity.

According to another aspect of the present invention, a toner concentration of a liquid developer including toner particles and carrier liquid is controlled. The carrier liquid is separated from the liquid developer and a developer electrical conductivity and a carrier liquid electrical conductivity are detected. An attribute value reflecting the toner concentration is detected from a difference of the developer electrical conductivity and a carrier liquid electrical conductivity and is compared to a predetermined value. When the attribute value is lower than the predetermined value, toner particles are supplied to the liquid developer.

The carrier liquid may be separated from the liquid developer using a filter for filtering out the toner particles from the liquid developer. The filter may be a semipermeable membrane.

As described above, the carrier liquid is separated from the liquid developer and a developer electrical conductivity and a carrier liquid electrical conductivity are detected. Based on the difference of these conductivities, the toner concentration is obtained. Therefore, the measurement of the toner concentration is unaffected by an increase in the number of ionic contaminants or the like due to deterioration of liquid developer, resulting in accurate and stable toner concentration detection.

Further, since the attribute value reflecting the toner concentration is used to control the toner concentration of the liquid developer, the toner concentration control is optimally performed with stability and reliability.

DETAILED DESCRIPTION OF THE PREFERRED EMBODIMENTS

Figure 1:
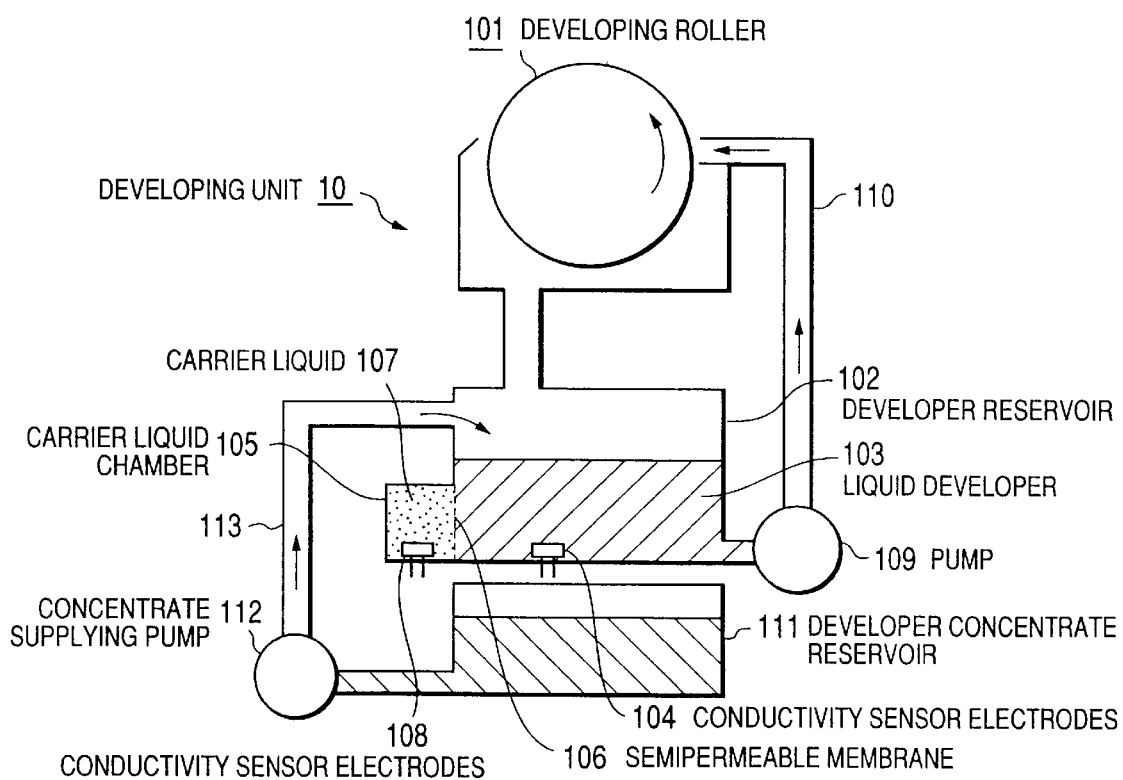
FIG. 1 is a schematic diagram showing the construction of a developing unit employing a toner concentration control system according to an embodiment of the present invention.

Referring to FIG. 1, a developing unit 10 is composed of a developing roller 101 which is opposite to a photoconductor (not shown) and a developer reservoir 102 which stores liquid developer 103. Reservoir 102 has a set of electrodes 104 therein which are connected to a developer conductivity sensor (shown in FIG. 2). The liquid developer 103 includes carrier liquid and toner particles and further includes ionic contaminants. More specifically, the liquid developer 103 is composed of a solvent, a charge controller, toner particles and ionic contaminants which would be mixed when combined with toner particles. The solvent may be normal paraffin hydrocarbon, isoparaffin hydrocarbon, or a derivative thereof.

The developer reservoir 102 is coupled to a carrier liquid chamber 105 through a filter member 106 which is a semipermeable membrane in this embodiment. In other words, a reservoir is separated into the developer reservoir 102 and the carrier liquid chamber 105 by the semipermeable membrane 106. The carrier liquid chamber 105 is located at a lowest position on the side wall of the developer reservoir 102. The carrier liquid chamber 105 has a set of electrodes 108 therein which are connected to a carrier liquid conductivity sensor (not shown).

The semipermeable membrane 106 can pass small particles such as ionic contaminants but blocks large particles such as toner particles. Since the liquid developer 103 includes toner particles and carrier liquid including ionic contaminants, the carrier liquid 107 including ionic contaminants is stored in the carrier liquid chamber 105. In other words, the semipermeable membrane 106 serves as a filter for filtering out toner particles from the liquid developer 103.

The liquid developer 103 is supplied to the developing roller 101 by a pump 109 through a developer supplying line 110. An excess of the liquid developer flows back to the developer reservoir 102. Since some toner particles are transferred to the developing roller 101 and then to the photoconductive drum, the toner concentration of the liquid developer 103 stored in the developer reservoir 102 is gradually decreased.

The developing unit 10 is further provided with a developer concentrate reservoir 111 for storing concentrated liquid developer. The concentrated liquid developer is supplied to the developer reservoir 102 by a concentrate supplying pump 112 through a developer concentrate supplying line 113. As will be described, when it is determined that the toner concentration is lower than a predetermined value, the concentrate supplying pump 112 is driven to supply the concentrated developer to the developer reservoir 102 so as to increase the toner concentration.

There may be provided a stirring means (not shown in FIG. 1) in the developer reservoir 102 to stirring the liquid developer 103.

Figure 2:
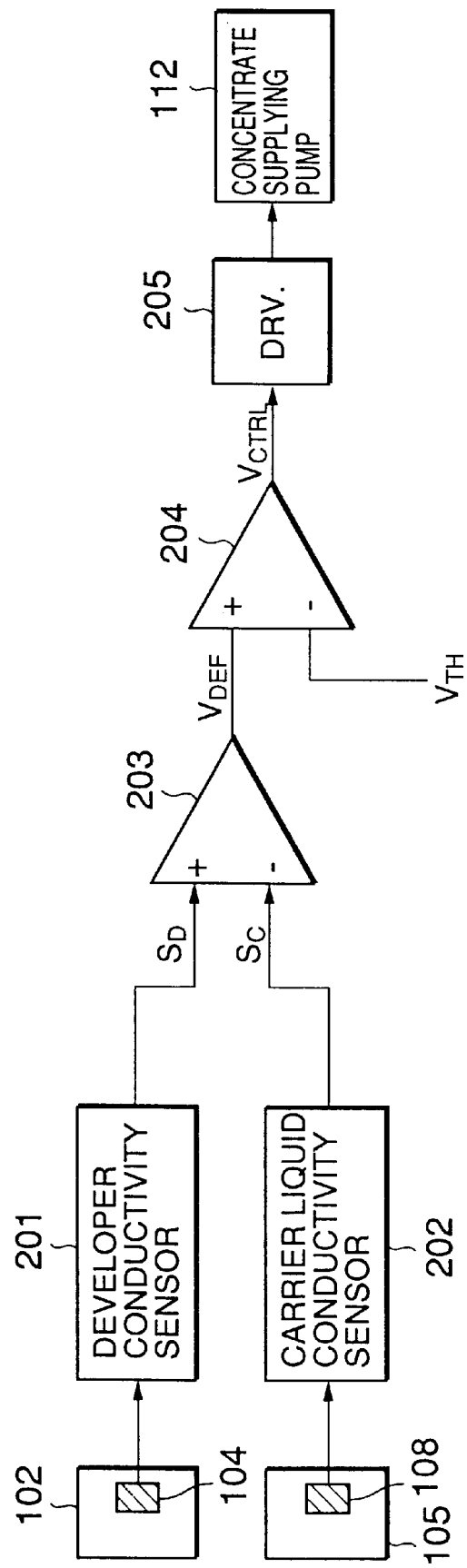
FIG. 2 is a block diagram showing the toner concentration control system according to the embodiment.

Referring to FIG. 2, the developer conductivity sensor 201 is comprised of an alternating current impedance measurement device which is provided with the set of electrodes 104 placed within the developer reservoir 102. Similarly, the carrier liquid conductivity sensor 202 is comprised of an alternating current impedance measurement device which is provided with the set of electrodes 108 placed within the carrier liquid chamber 105. Various well-known impedance measuring methods may be used such as using voltage and current meters and using a bridge circuit. The respective frequencies used in the sensors 201 and 202 are determined depending on the frequency response of the liquid developer 103 and the carrier liquid 107. As described above, the carrier liquid 107 stored in the carrier liquid chamber 105 does not include the toner particles but does include the solvent, the charge controller and ionic contaminants. Because the toner particles are filtered out by the semipermeable membrane 106.

The control system is comprised of a differential amplifier 203 which receives detected conductivity signals $S_D$ and $S_C$ from the sensors 201 and 202, respectively, and outputs a difference voltage $V_{DEF}$ to a comparator 204.

As described before, the developer reservoir 102 stores the liquid developer 103 including toner particles and carrier liquid and the carrier liquid chamber 105 stores the carrier liquid 107 including the charge controller and ionic contaminants. Therefore, the difference of the developer conductivity signal $S_D$ and the carrier liquid conductivity signal $S_C$ reflects a conductivity caused by toner particles included in the developer 103. In other words, the difference voltage $V_{DEF}$ reflects the toner concentration of the developer 103 and therefore the difference voltage $V_{DEF}$ can be used as the toner concentration of the developer 103.

The comparator 204 compares the difference voltage $V_{DEF}$ to a predetermined threshold voltage $V_{TH}$. When the difference voltage $V_{DEF}$ is greater than the predetermined threshold voltage $V_{TH}$, a pump control signal $V_{CTRL}$ is output to a driver 205 which drives the concentrate supplying pump 112.

The same toner concentration control as shown in FIG. 2 may be performed by a program-controlled processor running a control program. For example, a processor is connected to the developer conductivity sensor 201 and the carrier liquid conductivity sensor 202 and further to the driver 205.

Figure 3:
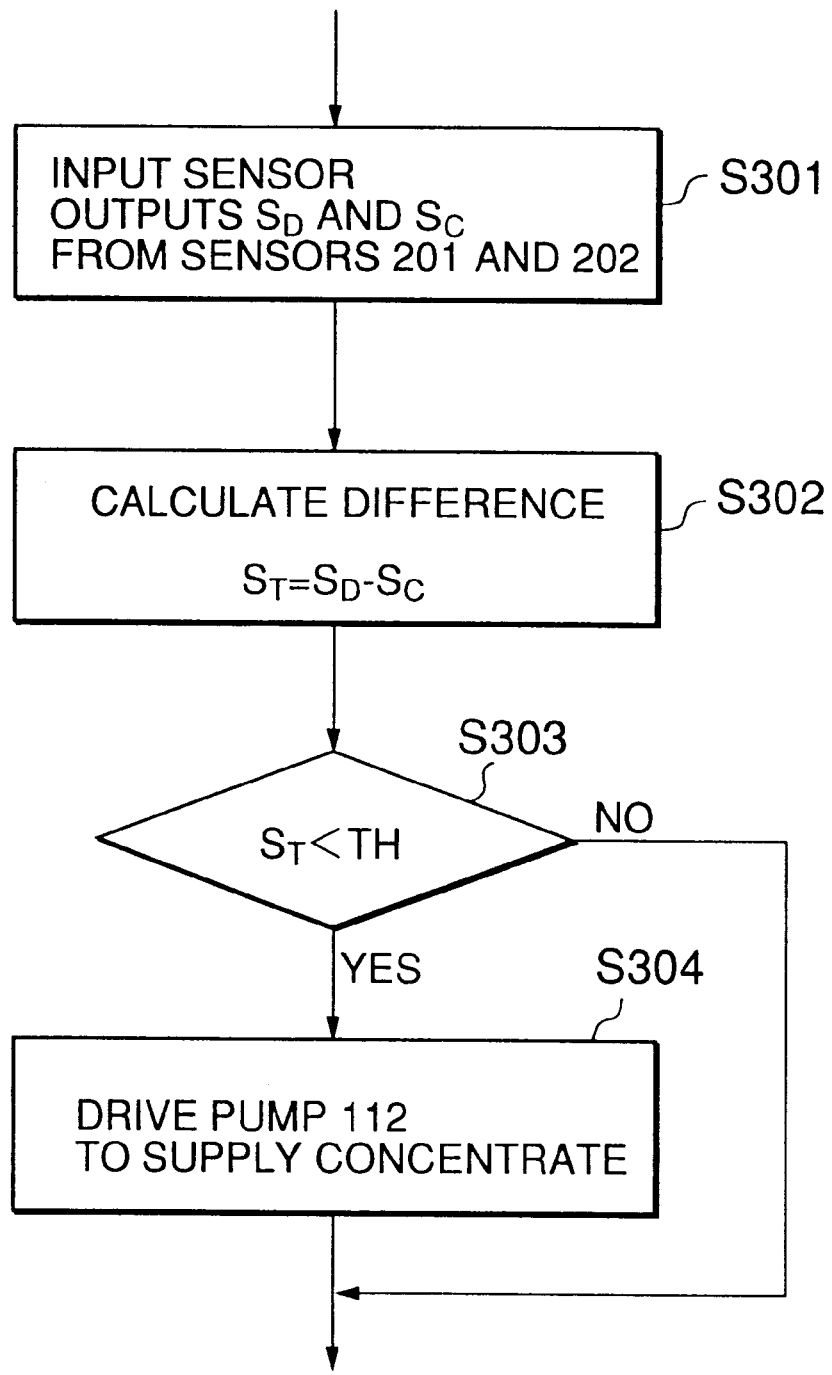
FIG. 3 is a flow chart showing a control flow of the toner concentration control system according to another embodiment of the present invention.

Referring to FIG. 3, the processor inputs the detected conductivity signals $S_D$ and $S_C$ from the sensors 201 and 202, respectively (step S301), and then calculates a difference $S_T$ of the conductivity signals $S_D$ and $S_C$ (step S302). If the difference $S_T$ is smaller than a predetermined threshold value TH (YES in step S303), the processor controls the driver 205 so that the concentrate supplying pump 112 supplies the concentrated liquid developer from the developer concentrate reservoir 111 to the developer reservoir 102 and the toner concentration of the developer 103 is increased (step S304). The amount of the supplied concentrated liquid developer may be determined depending on the difference of $S_T$ and the TH. In this manner, the toner concentration of the developer 103 is optimally kept.

What is claimed is:

1. A method for determining a toner concentration of a liquid developer including toner particles and carrier liquid, comprising the steps of:

separating the carrier liquid from the liquid developer;
   detecting a developer electrical conductivity and a carrier liquid electrical conductivity; and
   determining the toner concentration using a difference between the developer electrical conductivity and the carrier liquid electrical conductivity.

2. The method according to claim 1, wherein the carrier liquid is separated from the liquid developer using a filter for filtering out the toner particles from the liquid developer.

3. The method according to claim 2, wherein the filter is a semipermeable membrane.

4. The method according to claim 1, wherein the developer electrical conductivity is detected using an impedance measurement device having a plurality of electrodes provided in the liquid developer and the carrier liquid electrical conductivity is detected using another impedance measurement device having a plurality of electrodes provided in the carrier liquid.

5. A control method for controlling a toner concentration of a liquid developer including toner particles and carrier liquid, comprising the steps of:

separating the carrier liquid from the liquid developer;
   detecting a developer electrical conductivity and a carrier liquid electrical conductivity;
   determining the toner concentration using an attribute value that is a function of a difference between the developer electrical conductivity and the carrier liquid electrical conductivity;
   comparing the attribute value to a predetermined value; and
   supplying toner particles to the liquid developer when the attribute value is lower than the predetermined value.

6. The control method according to claim 5, wherein the carrier liquid is separated from the liquid developer using a filter for filtering out the toner particles from the liquid developer.

7. The control method according to claim 6, wherein the filter is a semipermeable membrane.

8. The control method according to claim 5, wherein the developer electrical conductivity is detected using an impedance measurement device having a plurality of electrodes provided in the liquid developer and the carrier liquid electrical conductivity is detected using another impedance measurement device having a plurality of electrodes provided in the carrier liquid.

9. The control method according to claim 5, wherein the toner particles are supplied to the liquid developer as a function of a difference between the attribute value and the predetermined value.

10. An apparatus for determining a toner concentration of a liquid developer including toner particles and carrier liquid in electrophotographic equipment, comprising:

a reservoir separated into a first chamber and a second chamber by a filter separating the carrier liquid from the liquid developer so that the first chamber stores the liquid developer and the second chamber stores the carrier liquid separated from the liquid developer;
    a detector detecting a developer electrical conductivity of the liquid developer stored in the first chamber and a carrier liquid electrical conductivity of the carrier liquid stored in the second chamber; and
    a comparator determining the toner concentration based on a difference between the developer electrical conductivity and the carrier liquid electrical conductivity.

11. The apparatus according to claim 10, wherein the first chamber is coupled to the second chamber through an opening where the filter is provided.

12. The apparatus according to claim 10, wherein the filter is a semipermeable membrane.

13. The apparatus according to claim 10, wherein the detector comprises:
- a first detector detecting the developer electrical conductivity using an impedance measurement device having a plurality of electrodes provided within the first chamber; and
- a second detector for detecting the carrier liquid electrical conductivity using another impedance measurement device having a plurality of electrodes provided within the second chamber.

14. A system for controlling a toner concentration of a liquid developer including toner particles and carrier liquid in electrophotographic equipment, comprising:
- a reservoir separated into a first chamber and a second chamber by a filter separating the carrier liquid from the liquid developer so that the first chamber stores the liquid developer and the second chamber stores the carrier liquid separated from the liquid developer;
- a concentrate reservoir storing a concentrated developer;
- a supplying pump supplying the concentrated developer to the first chamber;
- a detector detecting a developer electrical conductivity of the liquid developer stored in the first chamber and a carrier liquid electrical conductivity of the carrier liquid stored in the second chamber;
- a comparator determining an attribute value that is a function of the toner concentration using a difference between the developer electrical conductivity and the carrier liquid electrical conductivity; and
- a controller comparing the attribute value to a predetermined value and, when the attribute value is lower than the predetermined value, driving the supplying pump to supply the concentrated developer to the first chamber.

15. The system according to claim 14, wherein the first chamber is coupled to the second chamber through an opening where the filter is provided.

16. The system according to claim 14, wherein the filter is a semipermeable membrane.

17. The system according to claim 14, wherein the detector comprises:
- a first detector for detecting the developer electrical conductivity using an impedance measurement device having a plurality of electrodes provided within the first chamber; and
- a second detector for detecting the carrier liquid electrical conductivity using another impedance measurement device having a plurality of electrodes provided within the second chamber.

18. The system according to claim 14, wherein the concentrated developer is supplied to the first chamber as a function of a difference between the attribute value and the predetermined value.

* * * * *